United States Patent [19]

Fahn

[11] 4,190,672

[45] Feb. 26, 1980

[54] METHOD AND COMPOSITIONS OF TREATING PARKINSONISMS WITH LEVODOPA AND 3',4'-DIHYDROXY-2-METHYLISOPROPI-OPHENONE

[76] Inventor: Stanley Fahn, 155 Edgars La., Hastings-on-Hudson, N.Y. 10706

[21] Appl. No.: 939,036

[22] Filed: Sep. 1, 1978

[51] Int. Cl.² .................... A61K 31/12; A61K 31/195
[52] U.S. Cl. ...................................... 424/319; 424/331
[58] Field of Search ............................... 424/331, 319

[56] References Cited

U.S. PATENT DOCUMENTS

| | | | |
|---|---|---|---|
| 2,929,848 | 3/1960 | Woodruff et al. | 424/331 |
| 3,790,674 | 2/1974 | Rodriguez | 424/250 |
| 3,984,545 | 10/1976 | Fril, Jr. et al. | 424/319 |
| 3,991,207 | 11/1976 | Sarges et al. | 424/319 |

OTHER PUBLICATIONS

Chem. Abst., vol. 67-8134a (1967).

*Primary Examiner*—Stanley J. Friedman
*Attorney, Agent, or Firm*—Robert A. Armitage

[57] ABSTRACT

Improved methods are provided for the treatment of the central nervous system dopamine-deficiency diseases (CNS-DADD's), including Parkinson's disease and other parkinsonisms, which comprises the administration of 3',4'-dihydroxy-2-methyl-isopropiophenone (DHMPP) in an amount effective to inhibit the conversion of levodopa to 3-O-methyldopa (OMD) by catechol-O-methyl transferase (COMT). The present method results in a reduction of the dosage of levodopa otherwise required to symptomatically control the CNS-DADD, providing a concomitant reduction in the untoward side effects of levodopa administration. Also provided are novel pharmaceutical compositions of levodopa and DHMPP.

8 Claims, No Drawings

METHOD AND COMPOSITIONS OF TREATING PARKINSONISMS WITH LEVODOPA AND 3',4'-DIHYDROXY-2-METHYLISOPROPIOPHENONE

BACKGROUND OF THE INVENTION

1. Field of the Invention

The present invention relates to novel methods for the treatment of central nervous system dopamine-deficiency diseases (CNS-DADD's). The present invention further relates to improved methods of using levodopa in the treatment of a CNS-DADD. Also the present invention provides novel pharmaceutical compositions of levodopa and 3',4'-dihydroxy-2-methylpropiophenone (DHMPP).

The CNS-DADD's include classical Parkinson's disease (paralysis agitans) as well as other parkinsonisms. Such other parkinsonisms include, for example, post-encephalitic parkinsonism and symptomatic parkinsonism. The latter condition may, for example, occur following injury to the nervous system by chemical intoxication (e.g., with carbon monoxide and manganese).

Classical Parkinson's disease or paralysis agitans is characteristically a progressive disease which becomes manifest primarily in the elderly and is marked by a mask-like physiognomy, a characteristic tremor of the resting muscles, a slowing of voluntary movements, a festinating (or accelerating) gait, peculiar posture, and muscular weakness. Parkinson's disease is occasioned by a neuroregulator (dopamine) deficiency or depletion in the central nervous system in the sense that increasing CNS dopamine levels provides symptomatic relief to a patient. In Parkinson's disease, as well as other CNS-DADD's, administration of dopamine itself does not provide symptomatic relief, since the dopamine apparently does not cross the blood-brain barrier.

However, a metabolic precursor of dopamine, levodopa or 3-(3,4-dihydroxyphenyl)-L-alanine, does cross the blood-brain barrier and has long been recognized as effective in the alleviation of CNS-dopamine deficiency, thus providing symptomatic relief of the disease.

Biochemically, the transformation of levodopa to dopamine is accomplished enzymatically by dopa decarboxylase, i.e.:

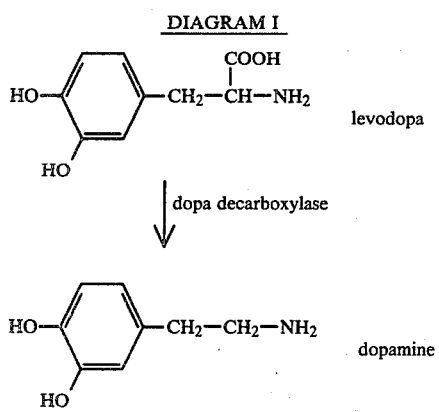

DIAGRAM I

Since dopa decarboxylase is present both within the central nervous system and outside of it (e.g., the peripheral nervous system), levodopa administered to a patient is rapidly converted to dopamine in extracerebral tissues. This requires that large doses of levodopa be administered in order to assure that effective doses of levodopa do indeed cross the blood-brain barrier. Accordingly, peripheral dopa decarboxylase inhibitors, i.e., extracerebral inhibitors of dopa decarboxylase, have been employed concomitantly with levodopa. Since such inhibitors act only in extracerebral tissues (i.e., do not cross the blood-brain barrier), they permit dopamine production in the central nervous system while preventing excessive and undesirable dopamine production outside the central nervous system. The use of the peripheral dopa decarboxylase inhibitor, by permitting much lower doses of levodopa, is beneficial in that a reduction in the adverse effects of levodopa administration (e.g., nausea and vomiting) is experienced.

3',4'-Dihydroxy-2-methyl-propiophenone (DHMPP) is known in the art to be useful in relieving dysmenorrhea, forestalling spontaneous abortion, and other conditions in which relaxation of uterine smooth muscle is indicated. Further, this compound is otherwise generally known as a muscle relaxant. See, for example, U.S. Pat. No. 2,929,484, describing its preparation and uses.

DHMPP is a compound of the following structural formula:

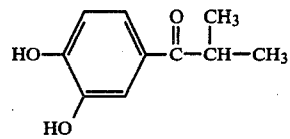

This compound, like levodopa and dopamine, is structurally a catechol in that it contains a vicinally dihydroxylated benzene group, i.e.,

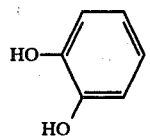

DHMPP is known to exhibit numerous other pharmacological effects. Some of these effects are reported in the following scientific references:

Moffett, R. B., et al., "Central Nervous System Depressants. V. Polyhydroxy and Methoxyphenyl Ketones, Carbinols, and Derivatives", J. Med. Chem. 7:178–186 (1964);

Miller, J. W., et al., "Potentiation of the Inotropic Actions of Certain Catecholamines by U-0521 (3,4-dihydroxy-alpha-methyl propiophenone) on the Isolated Atria of the Rabbit", Pharmacologist 8:203 (1966);

Giles, R. E., et al., "The Catechol-O-methyl Transferase Activity and Endogenous Catecholamine Content of Various Tissues in the Rat and the Effect of Administration of U-0521 (3,4-dihydroxy-2-methyl propiophenone)", J. Pharmacol. Exp. Ther. 158:189–194 (1967);

Trendelenburg, U., et al., "Influence of Block of Catechol-O-methyl Transferase on the Sensitivity of Isolated Organs to Catechol Amines", Naunyn-Schmiedeberg's Arch. Pharmacol. 271:59–92 (1971);

Bausher, L. P., et al., "Potentiation of the Effects of Topical Epinephrine on the Pupil and Intraocular Pressure in the Sympathetically Denervated Rabbit Eye by a Catechol-O-Methyl-transferase Inhibitor", Invest. Ophthalmol. 15:854–857 (1976);

Gillespie, J. S., et al., "Influence of Iproniazid and 3,4-Dihydroxy-2-Methylpropiophenone U-0521 on Uptake and Metabolism of Norepinephrine by Rabbit Colon", Naunyn-Schmiedeberg's Arch. Pharmacol. 293(Suppl):R3 (1976); and Kaumann, A. J., "Activation of Myocardial β-Adrenoreceptors by the Nitrogen-free Low Affinity Ligand 3',4'-Dihydroxy-alpha-methylpropiophenone (U-0521)", Naunyn-Schmiedeberg's Arch. Pharmacol. 296-228 (1977).

Among the pharmacological properties of DHMPP described above is the inhibition of the enzyme catechol-O-methyl transferase (COMT). COMT is effective in converting levodopa to 3-O-methyldopa, as indicated in Diagram II.

DIAGRAM II

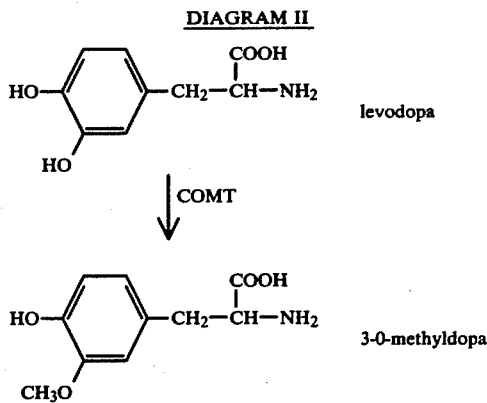

Absent the inhibition of COMT, levodopa is converted in part to 3-O-methyldopa (OMD) and the corresponding 3-O-methyldopamine (OMDA). To the extent that levodopa is converted to OMD and OMDA in vivo, it is not available for decarboxylation to dopamine, the active principle in the treatment of CNS-DADD's.

2. Prior Art

As indicated above, DHMPP is known in the art, as are numerous pharmacological actions of DHMPP, including its activity in the inhibition of COMT. See Giles, R. E., et al., J. Pharmacol. Exp. Ther., 158:189-194 (1967).

Also known in the art is the treatment of CNS-DADD's with levodopa and combinations of levodopa and a dopa decarboxylase inhibitor. See, for example, the description of the actions and indications of combinations of levodopa and carbidopa in Physicians' Desk Reference, 31st Ed., published by Medical Economics Company, 1977, page 1101.

Further the treatment of Parkinson's disease with combinations of levodopa and a COMT inhibitor is reported in the art. See Ericsson, A. D., J. Neurol. Sci. 14:193 (1971), reporting the use of N-butyl gallate. Further, for a review of other COMT inhibitors, including a discussion of their toxicity, see Angel, A., et al., Nature 217:84 (1968) and Guldberg, H. C., et al., Pharm. Rev. 27:135 (1975).

Finally, for a discussion of the relative levels of levodopa and OMD in CNS-DADD patients, see Muenter, N. D., et al., Mayo Clin. Proc., 47:389 (1972), Fahn, S., Neurology 24:431 (1974), and Sharpless, N. S., et al., Clin. Chim. Acta. 31:155 (1971). The correlation of high plasma levels of OMD with dopa-induced impairment of voluntary movements (dyskinesias) is reported in Rivera-Calimlin, L., et al., Arch. Neurol. 34:228 (1977) and Fuerstein, C., et al., Acta. Neurol. Scandinav. 56:79 (1977).

SUMMARY OF THE INVENTION

The present invention provides novel methods for the treatment of central nervous system dopamine deficiency diseases (CNS-DADD's).

The present invention further provides improvements in the use of levodopa, or the use of levodopa in combination with a peripheral dopamine decarboxylase inhibitor, in the treatment of CNS-DADD's.

The present invention further provides a method for reducing the dosage of levodopa which is effective in the symptomatic treatment of CNS-DADD's.

Further, the present invention provides a method for the concomitant administration of levodopa and a catechol-O-methyl transferase (COMT) inhibitor, 3',4'-dihydroxy-2-methyl-isopropiophenone (DHMPP), resulting in surprisingly and unexpectedly improved results (i.e., reduction of untoward effects of levodopa administration) in the symptomatic treatment of the CNS-DADD.

Lastly the present invention provides novel pharmaceutical compositions of levodopa and DHMPP.

In particular, the present invention provides (a) in a method of treating a CNS-DADD, which consists essentially of administering systemically to a human suffering from said CNS-DADD either (1) levodopa or (2) levodopa and a peripheral dopa decarboxylase inhibitor, the improvement which comprises:
concomitantly systemically administering to said human an amount of 3',4'-dihydroxy-2-methyl-isopropiophenone (DHMPP) effective to inhibit in vivo the conversion of levodopa to 3-O-methyldopa by catechol-O-methyl transferase (COMT);

(b) a method of treating a CNS-DADD in a human suffering from said CNS-DADD which comprises:
(1) systemically administering to said human an amount of 3',4'-dihydroxy-2-methyl-isopropiophenone (DHMPP) effective to inhibit in vivo the conversion of levodopa to 3-O-methyldopa by catechol-O-methyl transferase (COMT); and
(2) concomitantly systemically administering to said human an amount of levodopa effective to control the symptoms of said CNS-DADD;

(c) a method of reducing the dosage of levodopa required for the effective symptomatic treatment of a CNS-DADD in a human suffering from said CNS-DADD, which comprises:
concomitantly administering to said human an amount of 3',4'-dihydroxy-2-methyl-isopropiophenone (DHMPP) effective to inhibit in vivo the conversion of levodopa to 3-O-methyldopa by catechol-O-methyl transferase (COMT);

(d) a solid pharmaceutical composition for the treatment of a CNS-DADD in a human suffering from said CNS-DADD in a unit dosage form comprising
(1) an amount of 3',4'-dihydroxy-2-methyl-isopropiophenone (DHMPP), which is effective to inhibit in vivo the conversion of levodopa to 3-O-methyldopa by catechol-O-methyl transferase (COMT) when systemically administered to said human, and
(2) an amount of levodopa effective to control the CNS-DADD symptoms when concomitantly systemically administered to said human with said amount of DHMPP; and (e) a liquid pharmaceutical composition for the treatment of a CNS-DADD comprising
  (1) 3',4'-dihydroxy-2-methyl-propiophenone (DHMPP) and
  (2) levodopa; in a weight ratio which is the fraction whose numerator is
    (a) the amount of a daily dosage of DHMPP effective to inhibit in vivo the conversion of levodopa to 3-O-methyldopa by catechol-O-methyl transferase (COMT) when systemically administered to said human; and whose denominator is
    (b) the amount of a daily dosage of levodopa effective to control the symptoms of said CNS-DADD when concomitantly systemically administered to said human with said amount of a unit dosage of DHMPP.

For the purposes of the present invention, the term "CNS-DADD" refers to each of the various central nervous system disorders or neurologies which are symptomatically responsive to treatment with levodopa. Thus, the term "CNS-DADD" refers not only to classical Parkinson's disease, but to other parkinsonisms and related neurological conditions.

3',4'-Dihydroxy-2-methyl-isopropiophenone (DHMPP) refers to the compound described and claimed in U.S. Pat. No. 2,929,848, issued Mar. 22, 1960. As indicated in U.S. Pat. No. 2,929,848, this compound can be prepared as a water-soluble white crystalline solid with a melting point 94.5°–95.5° C.

In accordance with the present invention, there is administered to a human suffering from a CNS-DADD an amount of DHMPP effective to inhibit in vivo the conversion of levodopa to 3-O-methyl levodopa by catechol-O-methyl transferase (COMT). The present invention therefore contemplates that the administration of DHMPP will be accomplished by any systemic route which is convenient and readily accessible to the attending physician. While all of the various conventional routes of administration are contemplated (e.g., intramuscular, subcutaneous, intravenous, vaginal, rectal, buccal and oral), the preferred route of administration is orally by means of a convenient oral dosage form. By this preferred embodiment, an oral dosage form, either solid (e.g., compressed tablets or gelatin capsules) or liquid (syrups or elixirs), is prepared by conventional methods. Most preferably, simple compressed tablets containing DHMPP, alone or together with levodopa, is prepared.

The present invention further contemplates the use of DHMPP as an adjunct to conventional CNS-DADD therapy with levodopa, specifically providing for the administration of DHMPP concomitantly with levodopa. In accomplishing the purposes of the present invention "concomitant" administration refers to the administration of the two agents (i.e., levodopa and DHMPP) in any manner in which the pharmacological effects of both are manifest in the CNS-DADD patient at the same time. Thus concomitant administration does not require that a single pharmaceutical composition, the same dosage form, or even the same route of administration be used for administration of both levodopa and DHMPP or that the two agents be administered at precisely the same time. However, the concomitant administration will be accomplished most conveniently by the same dosage form and the same route of administration, at substantially the same time. Obviously, the concomitant administration most advantageously proceeds by the administration of levodopa and DHMPP simultaneously in a novel pharmaceutical composition in accordance with the present invention.

The present invention further provides that the amount of DHMPP to be administered to a CNS-DADD patient be effective to inhibit in vivo the conversion of levodopa to OMD by COMT. Just as doses of levodopa must be carefully titrated in a CNS-DADD patient, the amount of DHMPP effective to inhibit COMT conversion must likewise be carefully titrated on a patient-by-patient basis, taking into account the age, weight, condition, sex and severity of the CNS-DADD. Equally importantly, the CNS-DADD patient's prior therapy must be evaluated (e.g., the established levodopa dosage and use of a dopa decarboxylase inhibitor), in order to establish the extent by which the dose of levodopa must be diminished as DHMPP therapy is initiated. By a preferred embodiment, for example, the effective COMT-inhibitory dose of DHMPP is determined by initiating concomitant treatment at low dosages of both DHMPP and levodopa and thereafter increasing dosages of both substances while monitoring patient response. When the dosage of DHMPP is fully inhibitory with respect to COMT, the dosage thereof should be maintained so long as it is well tolerated by the patient, but not thereafter increased. Ordinarily the dosage which is fully inhibitory of COMT will be apparent functionally by the inability to adjust a fully effective levodopa dosage downward when dosages of DHMPP are increased.

For a typical CNS-DADD patient the ultimate dosage of DHMPP which will effectively inhibit conversion by COMT is on the order of 6–10 g of DHMPP per day intravenously. When patient response in this dosage range is insufficient, somewhat higher doses of DHMPP are employed intravenously, ordinarily not in excess of 15 g per patient per day. When routes of administration other than intravenous routes are employed, the equivalent dosages to the aforementioned intravenous dosages are employed. Equivalent dosages refer to those dosages by routes other than intravenous administration whereby comparable systemic levels (e.g., blood levels) of DHMPP are obtained.

By the preferred route of administration (orally), the desired dosage is ordinarily provided in a unit dosage form periodically throughout the day. Accordingly, administration by the oral route at least twice daily is preferred, most preferably being at least four times daily. Thus, for example, for a patient whose oral dose is 10 g per day, four doses are provided each day most conveniently before or after each meal and before bedtime.

The novel pharmaceutical compositions in accordance with the present invention are prepared by conventional means by methods known in the art. For example, there are known in the art methods for the preparation of levodopa pharmaceutical compositions, fully adaptable to the preparation of compositions of both levodopa and DHMPP. Solid pharmaceutical compositions are provided in accordance with the present invention in the unit dosage form. A unit dosage for a solid pharmaceutical composition refers to the amount of each of the active ingredients which is administered in any one entity. Thus, the unit dosage form of a solid pharmaceutical composition makes reference to a discreet entity (e.g., a capsule, tablet, suppository, or drug-releasing device), one or more of which entities contains an appropriate dosage for a single administration. Typically, the unit dosage form of a solid pharmaceutical composition in accordance with the present invention will contain 500 mg of DHMPP and 50 mg of levodopa, with the ratio of these two agents varying from about 5:1 to about 25:1. When a total daily dose of 10 g of DHMPP and 1 g of levodopa is desired, five tablets each may be administered four times daily. For the novel solid pharmaceutical compositions wherein the ratio of DHMPP and levodopa is as high as about 25:1, the desired daily dosage of levodopa may be obtained by supplementation with formulations containing only levodopa as an active ingredient.

Accordingly, the novel solid pharmaceutical compositions in accordance with the present invention are adaptable to provide administration by oral, vaginal, rectal, and buccal routes of administration. However, for parenteral routes (e.g., subcutaneous, intravenous, and intraarterial) the novel liquid pharmaceutical compositions in accordance with the present invention are provided. Also provided are novel liquid pharmaceutical compositions suitable for oral administration (e.g., syrups and elixirs). Each of these novel liquid pharmaceutical compositions in accordance with the present invention is prepared by methods known in the art.

For the liquid pharmaceutical compositions the active agents, DHMPP and levodopa, are provided in the same weight ratio as the intended respective daily dosages thereof for the patient being treated. Accordingly, the weight ratio of levodopa to DHMPP are for such novel liquid pharmaceutical compositions falls within the same range indicated above for the solid pharmaceutical compositions (e.g., 1:5 to 1:25).

As a result of the employment of novel methods and compositions in accordance with the present invention, there is obtained surprisingly and unexpectedly improved results in the symptomatic treatment of CNS-DADD patients with levodopa. In particular, the present invention substantially eliminates the conversion of levodopa in vivo to 3-O-methyl levodopa. Thus, more of administered dose of levodopa is available systemically for transport across the blood-brain barrier and conversion in the central nervous system to dopamine. Hence, smaller doses of levodopa are employed in accordance with the present invention than are required under conventional treatment with levodopa alone or levodopa in combination with a peripheral dopa decarboxylase inhibitor. Hence the undesirable side effects of levodopa administration are minimized, while the untoward effects of 3-O-methyl dopa are substantially eliminated.

The instant use of DHMPP also provides surprisingly and unexpectedly improved results as compared to prior methods of treatment of CNS-DADD's with combinations of levodopa and COMT inhibitors. In particular, the present invention yields a surprisingly and unexpectedly decreased toxicity from the concomitant therapy as compared to that achieved by prior art methods.

DESCRIPTION OF THE PREFERRED EMBODIMENTS

EXAMPLE 1

The inhibition of OMD production during concomitant administration of DHMPP and levodopa.

The inhibition of OMD production during combination therapy with levodopa and DHMPP is determined in the following experiment.

A. Methods

Male Sprague-Dawley rats weighing 200–300 g are fasted for 17 hours prior to the experiments. They are kept for at least two days on a day-light, night-dark cycle, and the experiments are conducted between 0900 and 1400 hours on the day following the fast. All injections are given intraperitoneally, and all drugs are given as a suspension in 1% methyl ceullulose.

1. Effect of DHMPP with time: Absolute control rats receive no injections. Levodopa controls are given levodopa, 250 mg/kg. Experimental animals are pretreated with DHMPP, 250 mg/kg, 30 min before receiving a combined injection of DHMPP and levodopa, each 250 mg/kg. Animals are decapitated at 30 min time intervals between 0 and 120 min after levodopa administration. Blood and brain are collected.

2. Effect of dose of DHMPP: Absolute and levodopa control rats receive the same treatment as described above. Experimental rats were pretreated with DHMPP (50, 100, 150, 200 or 250 mg/kg) 30 min before receiving the injection of levodopa, 250 mg/kg. All animals are decapitated 90 min after receiving levodopa. Blood and brain are collected.

3. Analytical procedures: Brains are chilled on ice, homogenized in 3 volumes ice-cold 0.4 M perchloric acid containing 0.025% ascorbic acid, and centrifuged at 15,000 rpm for 20 min. The supernatants are collected and the above procedure is repeated on the residue. The combined supernatants are stored at $-20°$ C. Blood samples are collected in heparinized tubes immediately after decapitation, chilled, and centrifuged, and the plasma is pipetted off. Plasma proteins are precipitated in 4 volumes ice-cold 0.4 M perchloric acid solution and centrifuged at 10,000 rpm for 15 min. Protein-free supernatants are decanted and stored at $-20°$ C. All samples are chromatographed within two days of the experiment.

Column chromatography of the sample extracts is carried out on a strong cation resin (Bio Rad AG 50-X8) according to the method of Prased, A. L. N., et al., Trans. Am. Soc. Neurochem. 4:105 (1973) Homovanillic acid (HVA) remains in the combined effluent and subsequent water wash; these eluates undergo solvent extractions and are assayed by the automated method of Prasad, A. L. N., et al., Biochem. Med. 9:136 (1974). Levodopa and OMD are eluted together and assayed according to the method of Fahn, S., et al., Anal. Biochem. 46:557 (1972). After dopamine is eluted, it is measured by the automated method of Atack, C. V., Brit. J. Pharmacol. All eluates are assayed within 10 days of chromatography; they are stored at $-20°$ C., thawed and mixed thoroughly before assay.

B. Results

1. Behavioral responses: All rats treated with levodopa exhibit increased locomotor activity, erection of hair (piloerection), abnormal protrusion of the eyeball (exophthalmos) and other signs of sympathetic stimulation. Those treated with DHMPP show striking reduction in motor activity within 10 min of injection, including prostration, lying on one side, rapid breathing and loss of responsiveness to handling and other stimuli. The degree of lethargy is related to the dosage of DHMPP employed. Administration of levodopa markedly attenuates all lethargic symptoms induced by DHMPP, but does not abolish them. Little piloerection is apparent in animals receiving both inhibitor and levodopa. In the time-course experiment, in which the rats receive a total of 500 mg/kg of the inhibitor in two injections of 250 mg/kg, five of 20 animals die after receiving the second injection. In the dose-response experiment in which a single dose of the inhibitor is administered, two of six animals receiving 250 mg/kg die within 30 min, before receiving levodopa. Deaths do not occur with lower doses of DHMPP.

2. Effect of DHMPP with time: Maximal plasma levels of levodopa in rats treated with levodopa, alone or with DHMPP, occur 30 min after levodopa injection. Inhibition of COMT results in more than a three-fold increase in plasma levodopa levels and the peak plasma level occurs 90 min after levodopa administration.

After levodopa administration, the OMD progressively accumulates in plasma. OMD levels in plasma continue to increase for at least four hours after levodopa treatment. Treatment with DHMPP completely prevents measurable accumulation of OMD in plasma.

In brain of levodopa control rats, levodopa rises to a peak value 30 min after levodopa administration. With COMT inhibition levodopa concentration is increased more than two-fold at the 30 min time point, and continues to rise for an additional 30 min. Brain OMD levels rise slowly for the first 30 min in levodopa and absolute control animals and then increase more rapidly and linearly; levels were 18 nmoles/g 4 h after levodopa administration. The accumulation of brain OMD is blocked by DHMPP treatment.

Dopamine concentration in brain is maximal at 30 to 60 min after levodopa treatment in both groups of rats, but inhibition of COMT increases the level of dopamine more than two-fold at 60 min.

3. Effect of dose of DHMPP: A time point of 90 min after levodopa treatment is selected to evaluate the effect of dose of DHMPP on the accumulation of OMD. Plasma levodopa levels at this time point are not affected by treatment with DHMPP at 50-250 mg/kg. However, plasma OMD accumulation is completely blocked at doses of DHMPP of 100 mg/kg or greater. In brain, accumulation of OMD is inhibited by DHMPP doses of 100 and 200 mg/kg, respectively. Levodopa and dopamine levels in the brain are not significantly altered by DHMPP at the 90 min time point for all doses of DHMPP.

When the dose-response data for OMD in plasma and brain is plotted as percent inhibition relative to levodopa controls, the comparative effectiveness of DHMPP in preventing the accumulation of OMD is apparent. A dose of 100 mg/kg completely inhibits OMD accumulation in plasma and inhibits the accumulation of OMD in the brain by 80%.

C. Conclusions.

The results clearly indicate that DHMPP does inhibit the accumulation of 3-O-methylated derivatives of catechols in plasma and brain under the conditions of high dosage, acute levodopa administration. As a result of this in vivo inhibition of COMT, striking enhancement and prolongation of levodopa and dopamine concentrations in the brain are achieved in animals treated with DHMPP.

EXAMPLE 2

Compressed tablet of DHMPP (500 mg) and levodopa (50 mg).

Employing conventional techniques, compressed tablets of DHMPP (500 mg) and levodopa (50 mg) are prepared from the following constituents:

| Constituent | Amount |
| --- | --- |
| DHMPP | 500 mg |
| Levodopa | 50 mg |
| Starch USP | 0.43 gr |
| Sucrose USP | 0.18 gr |
| White Mineral Oil USP | 0.08 gr |
| Talc USP | 0.75 gr |
| Calcium Stearate | 0.75 gr |

In a manner similar to that described in Example 2, compressed tablets containing 250 mg of DHMPP and 50 mg of levodopa are prepared. When additional tablet bulk is desired, lactose USP (e.g., typically 1-4 grains) is added.

EXAMPLE 3

Sterile solution of DHMPP (25 mg/ml) and levodopa (2.5 mg/ml).

By conventional techniques, a sterile pharmaceutically acceptable solution for parenteral administration is prepared from the following constituents:

| Constituent | Amount |
| --- | --- |
| DHMPP | 25 mg |
| Levodopa | 2.5 mg |
| Sodium Metabisulfite | 1 mg |
| Benzyl Alcohol NF | 9 mg |
| N,N-dimethylacetamide | 10% by volume |
| Sterile, air-free water | q.s. to 1 ml |

Corresponding pharmaceutical compositions are prepared using variable ratios of DHMPP and levodopa by varying the levodopa content of Example 3.

I claim:

1. A method of treating a central nervous system dopamine deficiency disease (CNS-DADD) in a human suffering from said CNS-DADD which comprises:
  (1) systemically administering to said human an amount on the order of 6-10 grams per day intravenously, or an equivalent dosage by routes other than intravenous administration, of 3',4'-dihydroxy-2-methyl-isopropiophenone (DHMPP), an amount of DHMPP effective to inhibit in vivo the conversion of levodopa to 3-O-methyldopa by catechol-O-methyl transferase (COMT); and
  (2) concomitantly systemically administering to said human an amount of levodopa effective to control the symptoms of said CNS-DADD.

2. A method of reducing the dosage of levodopa required for the effective symptomatic treatment of a central nervous system dopamine deficiency disease (CNS-DADD) in a human suffering from said CNS-DADD which comprises:
  concomitantly administering to said human an amount on the order of 6-10 grams per day intravenously, or an equivalent dosage by routes other than intravenous administration, of 3',4'-dihydroxy-2-methyl-isopropiophenone (DHMPP), an amount of DHMPP effective to inhibit in vivo the conversion of levodopa to 3-O-methyldopa by catechol-O-methyl transferase (COMT).

3. A solid pharmaceutical composition for the treatment of a central nervous system dopamine deficiency disease (CNS-DADD) in a human suffering from said CNS-DADD in a unit dosage form comprising (1) an amount of 3′,4′-dihydroxy-2-methyl-isopropiophenone (DHMPP), which is effective to deliver a dosage on the order of 6–10 grams per patient per day intravenously, or an equivalent dosage by routes other than intravenous administration, an amount of DHMPP which is effective to inhibit in vivo the conversion of levodopa to 3-O-methyldopa by catechol-O-methyl transferase (COMT) when systemically administered to said human and (2) an amount of levodopa effective to control the CNS-DADD symptoms when concomitantly systemically administered to said human with said amount of DHMPP.

4. A compressed tablet or gelatin capsule according to claim 3.

5. A vaginal or rectal suppository according to claim 3.

6. A liquid pharmaceutical composition for the treatment of a central nervous system dopamine deficiency disease (CNS-DADD) comprising (1) 3′,4′-dihydroxy-2-methyl-propiophenone (DHMPP) and (2) levodopa; in a weight ratio which is the fraction whose numerator is:

(a) the amount of a unit dosage of DHMPP effective to deliver a dosage on the order of 6–10 grams per patient per day intravenously, or an equivalent dosage by routes other than intravenous administration, an amount of DHMPP which is effective to inhibit in vivo the conversion of levodopa to 3-O-methyldopa by catechol-O-methyl transferase (COMT) when systemically administered to said human; and whose denominator is (b) the amount of a unit dosage of levodopa effective to control the symptoms of said CNS-DADD when concomitantly systemically administered to said human with said amount of a unit dosage of DHMPP.

7. A sterile solution according to claim 6.

8. A syrup according to claim 6.

* * * * *